(12) United States Patent
Lee et al.

(10) Patent No.: US 9,897,562 B2
(45) Date of Patent: Feb. 20, 2018

(54) DRYNESS SENSING CIRCUIT AND SENSING METHOD OF DRYNESS

(71) Applicant: LG ELECTRONICS INC., Seoul (KR)

(72) Inventors: Hoonbong Lee, Seoul (KR); Junghun Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 289 days.

(21) Appl. No.: 14/735,654

(22) Filed: Jun. 10, 2015

(65) Prior Publication Data

US 2016/0209345 A1 Jul. 21, 2016

(30) Foreign Application Priority Data

Jan. 16, 2015 (KR) .................. 10-2015-0007746

(51) Int. Cl.
*D06F 58/28* (2006.01)
*G01N 27/04* (2006.01)

(52) U.S. Cl.
CPC ......... *G01N 27/048* (2013.01); *G01N 27/045* (2013.01); *D06F 2058/2819* (2013.01)

(58) Field of Classification Search
CPC ............. D06F 2058/2838; D06F 58/28; D06F 2058/2803; D06F 2058/2851; F26B 25/22; G01N 27/223
See application file for complete search history.

(56) References Cited

U.S. PATENT DOCUMENTS

| | | | | |
|---|---|---|---|---|
| 3,732,435 A * | 5/1973 | Strandberg, Jr. | ........ | F26B 25/22 307/118 |
| 5,943,198 A * | 8/1999 | Hirsh | ................... | H02H 11/005 361/103 |
| 6,466,270 B1 * | 10/2002 | Ichihara | ................ | H03L 7/0891 327/147 |
| 7,345,491 B2 * | 3/2008 | Pezier | ..................... | D06F 58/28 324/664 |
| 9,657,433 B2 * | 5/2017 | Doh | ....................... | D06F 58/28 |
| 2006/0242859 A1 * | 11/2006 | Pezier | ..................... | D06F 58/28 34/528 |
| 2014/0320153 A1 * | 10/2014 | Johnson | ............. | G01R 1/06788 324/713 |

FOREIGN PATENT DOCUMENTS

KR 10-1990-0008932 12/1990
KR 10-2007-0071898 7/2007

OTHER PUBLICATIONS

Korean Office Action for Application 10-2015-0007746 dated Dec. 16, 2015.

* cited by examiner

*Primary Examiner* — Alesa Allgood
(74) *Attorney, Agent, or Firm* — KED & Associates LLP

(57) ABSTRACT

A dryness sensing circuit and a dryness sensing method are provided. The dryness sensing circuit and the dryness sensing method set a time constant of a resistor and capacitor short for liquidity of dryness determination algorithm and minimize a noise effect of a power supply.

14 Claims, 14 Drawing Sheets

DRYNESS SENSING CIRCUIT AND SENSING METHOD OF DRYNESS

CROSS-REFERENCE TO RELATED APPLICATION(S)

The present application claims priority under 35 U.S.C. 119 and 35 U.S.C. 365 to Korean Patent Application No. 10-2015-0007746 filed in Korea on Jan. 16, 2015, which is hereby incorporated by reference in its entirety.

BACKGROUND

1. Field

The present disclosure relates to a dryness sensing circuit and a dryness sensing method.

2. Background

Typically, a clothes dryer is a device for automatically drying clothes in a wet state after washing and a kind thereof may be largely divided into a vented clothes dryer and a condensing clothes dryer.

Between them, a configuration of a vented clothes dryer is described as follows.

FIG. 1 illustrates a structure of a typical vented clothes dryer, and FIG. 2 illustrates a Euro structure of the dryer of FIG. 1. The existing clothes dryer includes a main body 1 having a door 2 formed in a front surface, a drum 3 rotatably installed inside the main body 1 and having a plurality of protruding lifters 4 in an inner circumferential surface, a driving means for granting torque to the drum 3, a heater 5 heating intake external air to a high temperature to generate hot wind, an intake duct 7 communicated with a rear side opening of the drum 3 and guiding the hot wind generated by the heater 5 inside he drum 3, a lint duct 8 communicated with a front opening of the drum 3 and guiding humid air emitted after drying to an exhaust duct 15, and a blower fan 13 installed at a rear side of the lint duct 8 and generating a blower force.

A filter 14 is installed at an inlet part of the lint duct 8, which filters foreign materials such as dust or lint from air emitted from the drum 3.

The driving means for rotating the drum 3 includes a motor 10 and a driving belt 12 connected to a driving pulley 11 coupled to the motor 10 and winding an outer circumference of the drum 3, and rotates the drum 3 according to rotation of the driving belt 12 wound around the driving pulley 11, when the driving pulley 11 rotates due to rotation of the motor 10.

Furthermore, an electrode sensor 30 is installed at the front side of the drum 3 in order to detect a dryness degree of dry target. The electrode sensor 30 includes two metal plates in parallel. When a dry target simultaneously contacts both metal plates, the electrode sensor 30 senses a dryness degree of clothes by using impedance generated both end of the electrode according to moisture containment of the dry target, and outputs the sensed result as a voltage signal. In addition, the dryness degree may be divided into a plurality of level (for example, very dry, more dry, normal, less dry, damp dry) according to the moisture containment. In this case, in the very level and the damp level, since a variation amount of the voltage signal is not great, which corresponds to a change of the impedance differed according to a change of the moisture containment of the dry target at both ends of the electrode, it is difficult to accurately measure the dryness degree of the dry target.

SUMMARY

Embodiments provide a dryness sensing circuit and a dryness sensing method capable of setting a time constant of a resistor and capacitor short for liquidity of dryness determination algorithm and minimizing a noise effect of a power supply.

Embodiments also provide a dryness sensing circuit and a dryness sensing method capable of using an operational amplifier of which an input impedance is very high for measuring a dryness of the dry target having larger resistance of several hundreds kΩ or higher and using a single power supply operational amplifier for cost reduction.

Embodiments also provide a dryness sensing circuit and a dryness sensing method of matching an optical element value to an internal element value for raising dryness resolution in a damp level.

Embodiments also provide a dryness sensing circuit and a dryness sensing method capable of adjusting a sensing voltage level in consideration of a measurement limit value of a measuring unit.

Embodiments also provide a dryness sensing circuit and a dryness sensing method capable of improving dryness capability by adjusting a sensing sensitivity of a dry level according to a dryness level.

In one embodiment, a dryness sensing circuit includes: a sensing electrode connected between first and second nodes; a non-inverting amplifier amplifying the first power supply voltage to output a first output voltage; a filter unit including at least one auxiliary electrode and a first filter resistor connected between the first node and a third node and connected to each other in serial, a filter capacitor connected between the third node and the ground, at least one second auxiliary electrode and second filter resistor connected between an output terminal of the non-inverting amplifier and the third node and connected to each other in serial, and a relay unit connected to each of the first and second auxiliary electrodes in parallel; and a voltage follower outputting a voltage of the third node as a second output voltage, wherein a dryness level of a dry target is sensed based on the second output voltage.

The relay unit may operate as a switch element short circuited or opened according to the dryness level of the dry target.

The relay unit may operate as a short circuited switch when moisture of the dry target is not smaller than a preset value, and the relay unit may operate as an open switch when the moisture of the dry target is smaller than the preset value.

The relay unit may sequentially operate as the short circuited switch according to reduction of the moisture contained in the dry target.

The non-inverting amplifier and the voltage follower may be single power supply operational amplifiers.

The non-inverting amplifier may receive the first power supply voltage through a non-inverting terminal, and may include first and second resistors connected to an inverting terminal and having an identical resistance value.

The dryness sensing circuit may further include a measurement unit measuring the second output voltage, wherein the first power supply voltage is a voltage value identical to a measurement limit value of the measurement unit.

The first filter resistor may have a value greater than 100 kΩ and not greater than 1.5 MΩ, the second filter resistor may have a value greater than 10 kΩ and not greater than 500 kΩ, and the filter capacitor may have a value of 0.01 μF.

The dryness sensing circuit may further include a protection unit including a first output resistor connected between an output terminal of the voltage follower and a fourth node, and a second output resistor connected between the fourth node and the ground.

The dryness sensing circuit may further include an output diode of which a cathode terminal is connected to a second power supplying terminal and an anode terminal is connected to the fourth node, and an output capacitor connected between the fourth node and the ground.

A second power supply voltage from the second power supply terminal may be identical to the first power supply voltage.

The dryness sensing circuit may further include a static electricity protection unit including a first capacitor and a first diac connected together in parallel and connected between the first node and the ground, and a second capacitor and a second diac connected to each other in parallel and connected between the ground and earth ground.

The dryness sensing circuit may further include a voltage limiting unit including a first diode of which a cathode terminal is connected to an output terminal of the non-inverting amplifier and an anode terminal is connected to the third node, and a second diode of which a cathode terminal is connected to the third node and an anode terminal is connected to the ground.

The details of one or more embodiments are set forth in the accompanying drawings and the description below. Other features will be apparent from the description and drawings, and from the claims.

BRIEF DESCRIPTION OF THE DRAWINGS

Embodiments will be described in detail with reference to the following drawings in which like reference numerals refer to like elements, and wherein.

DETAILED DESCRIPTION

Figure 1:
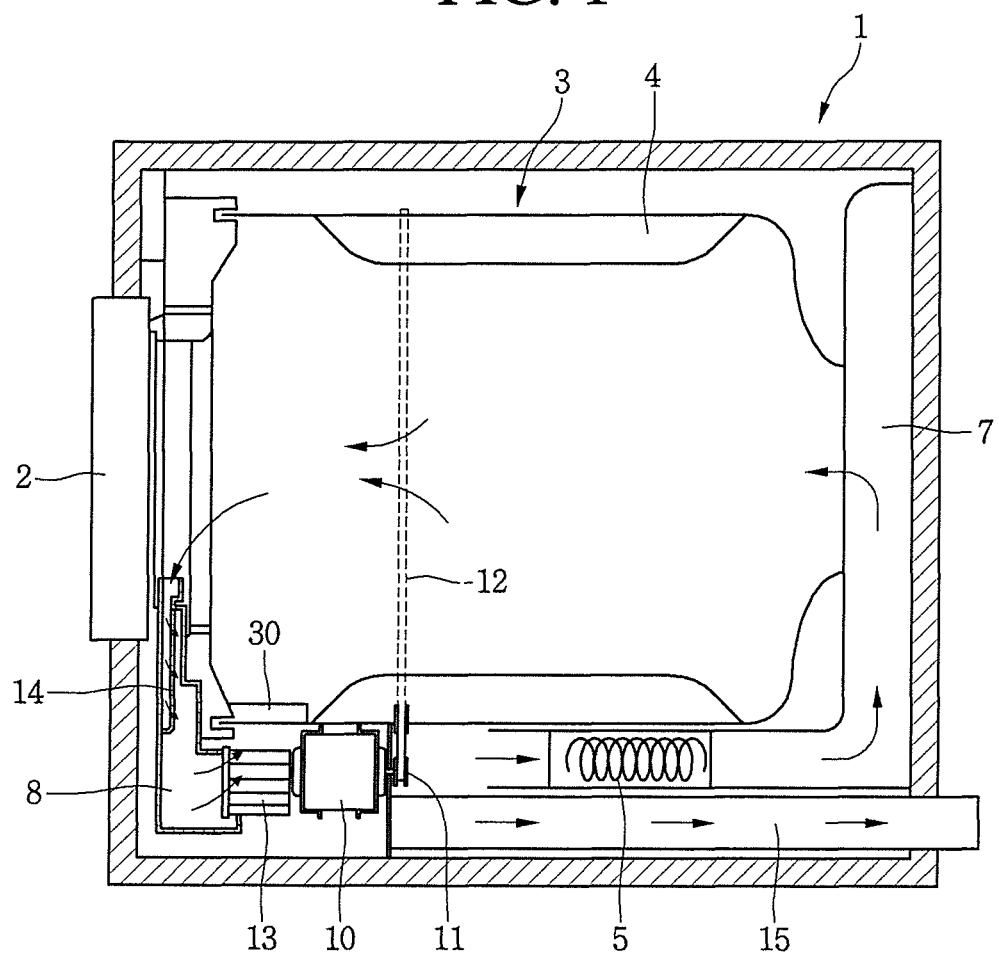
FIG. 1 illustrates a structure of a typical vented clothes dryer.
Figure 2:
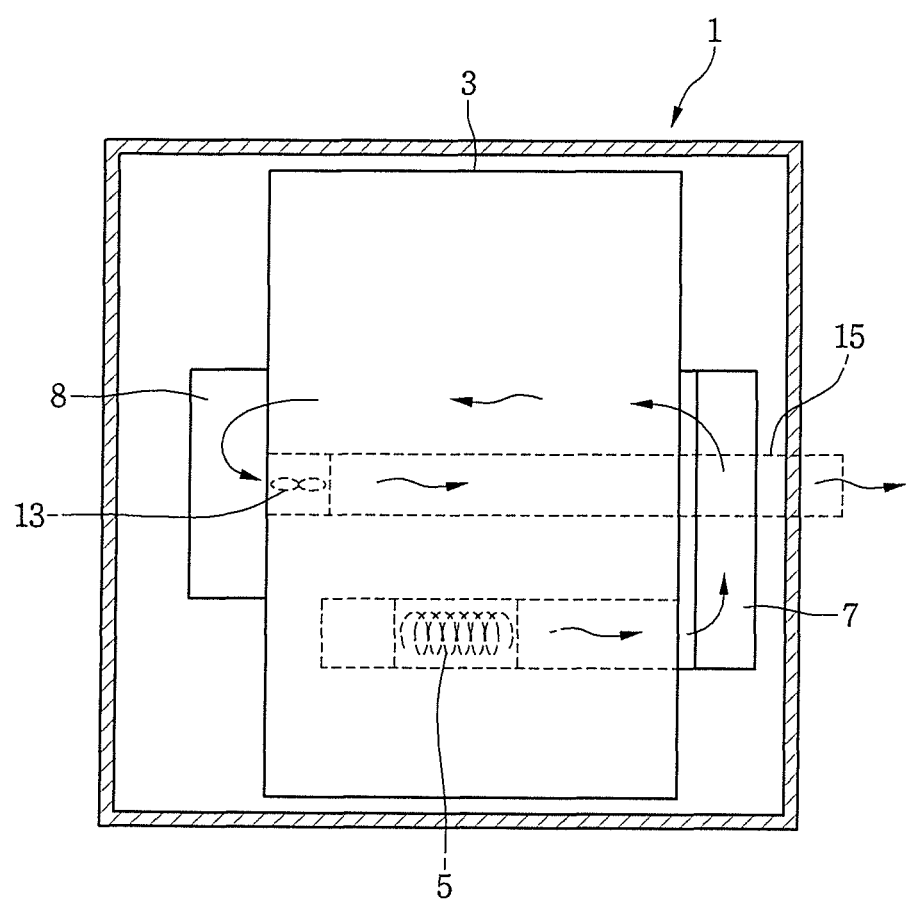
FIG. 2 illustrates a Euro structure of the dryer of FIG. 1.

Hereinafter, a dryness sensing circuit and a dryness sensing method according to embodiments will be described in detail with reference to the accompanying drawings. Following embodiments are provided as examples for sufficiently conveying the idea of the present invention to those skilled in the art. Accordingly, the present invention is not limited to the following embodiments but embodied in other types. In addition, sizes and thicknesses of elements in the drawings may be exaggerated for convenience of explanation. Like reference numerals refer to like elements throughout.

Advantages and features of the present invention, and methods for achieving the same will be cleared with reference to exemplary embodiments described later in detail together with the accompanying drawings. However, the present invention is not limited to the following exemplary embodiments, but realized in various forms. In other words, the present exemplary embodiments are provided just to complete disclosure the present invention and make a person having an ordinary skill in the art understand the scope of the invention. The present invention should be defined by only the scope of the accompanying claims. Throughout this specification, like numerals refer to like elements. In the drawings, sizes and relative sizes of layers and regions may be enlarged or exaggerated for clarity.

When an element or a layer is referred to as being 'on' another element or a layer, it can be directly on the other element or layer, or intervening elements or layers may also be present. In contrast, when an element is referred to as being "directly on" another element, there are no intervening elements present.

Spatially relative terms, such as "above," "upper," "beneath," "below," "lower," and the like, may be used herein for ease of description to describe one element or feature's relationship to other elements or features as illustrated in the figures. It will be understood that the spatially relative terms are intended to encompass different orientations of the device in use or operation in addition to the orientation depicted in the figures. For example, when elements drawn in the drawings are inverted, elements described as "below", or "beneath" another element may be disposed "above" the other element. Accordingly, the exemplary term "below" may include all directions of up and down.

The terms and words used in the following description and claims are to describe embodiments but are not limited the inventive concept. As used herein, the singular forms "a," "an" and "the" are intended to include the plural forms as well, unless the context clearly indicates otherwise. It will be further understood that the terms "comprises" and/or "comprising" used herein specify the presence of stated components, operations and/or elements but do not preclude the presence or addition of one or more other components, operations and/or elements.

<Dryness Sensing Circuit Diagram>

Figure 3:
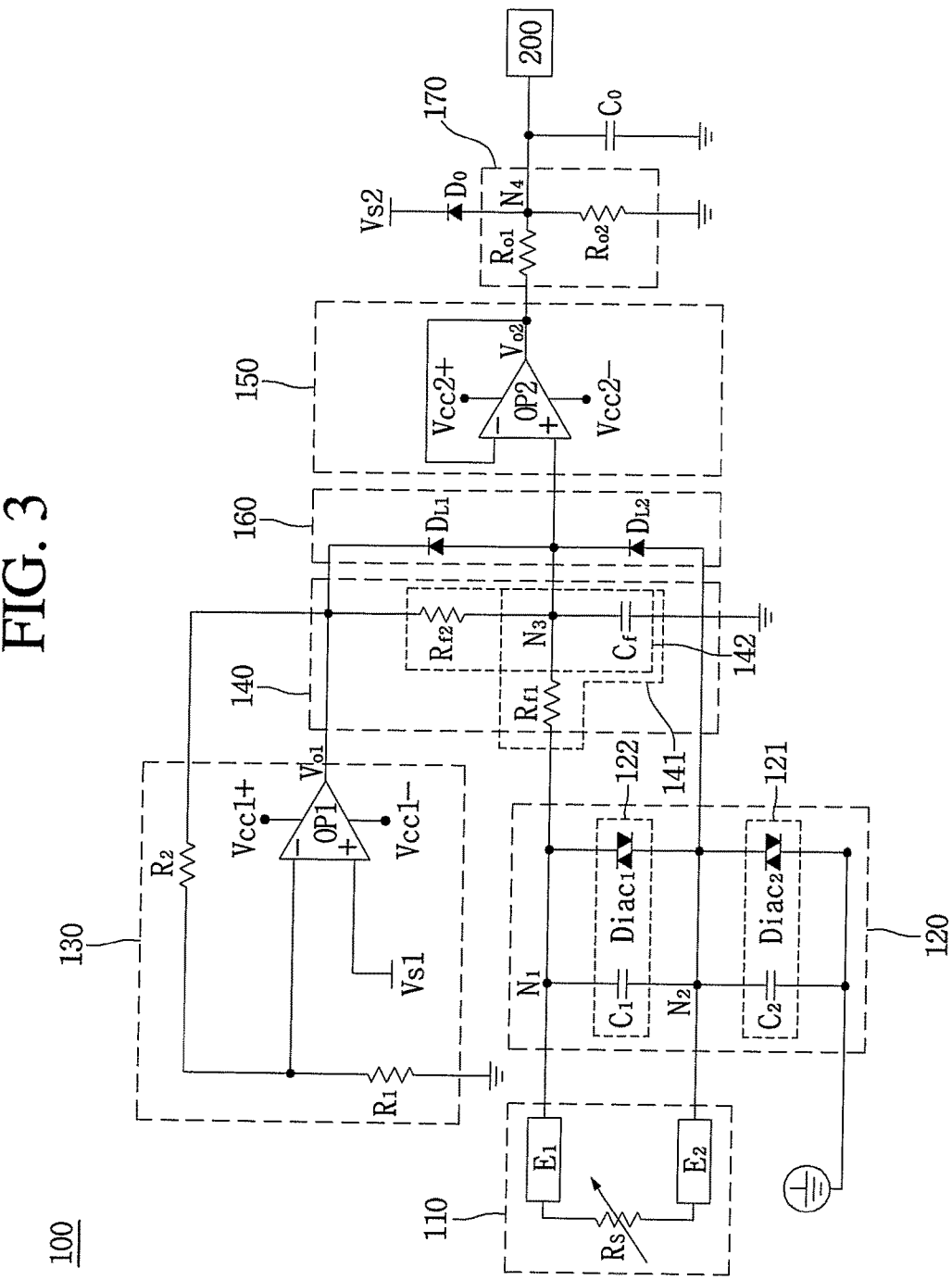
FIG. 3 is a circuit diagram according to a first embodiment.
Figure 4:
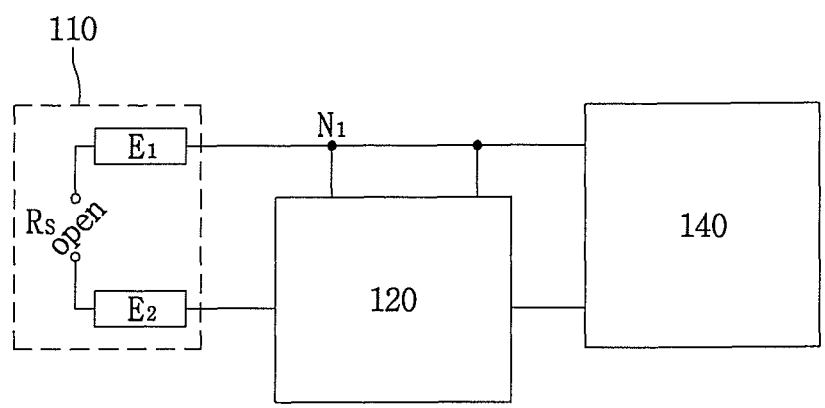
FIGS. 4 and 5 are circuit diagrams according to an operation of a sensing unit.
Figure 5:
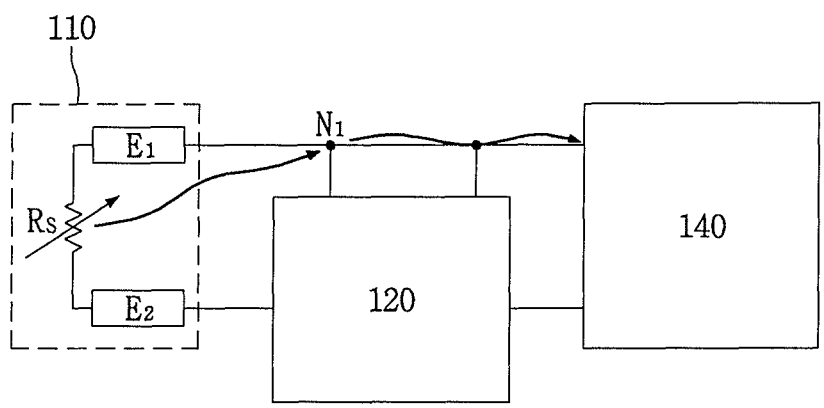

FIG. 3 is a dryness sensing circuit diagram according to a first embodiment, and FIGS. 4 and 5 are circuit diagrams according to an operation of a sensing unit.

Referring FIG. 3, a dryness sensing circuit 100 according to a first embodiment may include a sensing unit 110, a static electricity protection unit 120, a power supplying unit 130, a filter unit 140, an output unit 150, a voltage limiting unit 160, and a protection unit 170.

The sensing unit 110 includes first and second sensing electrodes E1 and E2, and a resistance value of a resistor between ends of the first and second sensing electrodes E1 and E2, namely, a sensing resistor Rs as an equivalent model may be varied according to an amount and wet degree of clothing which is a dry target contacting the first and second sensing electrodes E1 and E2. For example, a value of the sensing resistor Rs become equivalently infinite and both ends of the first and second sensing electrodes E1 and E2 operate as open circuits in a non-load state where the clothing does not exist or in a dry state where the clothing is completely dried. In addition, as shown in FIG. 5, when the clothing is in a wet state, the value of the sensing resistor Rs is changed according to a water content ratio and may be function as a variable resistor. Accordingly, the value of the sensing resistor Rs is varied according to an amount and wet degree of clothing and accordingly a sensing voltage, namely, a voltage of a first node N1, applied to the filter unit 140 may be differed.

The static electricity protection unit 120 includes first and second static electricity prevention circuits 121 and 122, the first static electricity prevention circuit 121 is connected between the earth ground and a second node N2, and the second static electricity prevention circuit 122 may be connected between the first node N1 and the second node N2. In addition, the first static electricity prevention circuit 121 includes a first capacitor C1 and a first diac diac 1 connected in parallel between the first and second nodes N1 and N2, and the second static electricity prevention circuit 122 includes a second capacitor and a second diac diac 2 connected in parallel between the second node N2 and the earth ground. In addition, the static electricity protection unit 120 may reduce noise flowing into the static electricity protection unit 120.

The power supplying unit 130 is a power supply voltage and may include a first operational amplifier OP1 capable of outputting a first output voltage Vo1, and first and second resistors R1 and R2 connected to the first operational amplifier OP1. The first operational amplifier OP1 and the first and second resistors R1 and R2 may be connected with each other to be a non-inverting operational amplifier. In detail, a first power supply voltage Vs1 is supplied to a non-inverting terminal+ of the first operational amplifier OP1, the first resistor R1 is connected between an inverting terminal– of the first operational amplifier OP1 and the ground, and the second resistor R2 is connected between the inverting terminal– of the first operation amplifier OP1 and an output terminal. In addition, the first operational amplifier OP1 may be driven by a first positive supplying voltage Vcc1+ and a first negative supplying voltage Vcc1–. In addition, the first negative supplying voltage Vcc1– may be 0 V. Therefore, the first operational amplifier OP1 may be driven as an operational amplifier for a signal power supply.

Furthermore, a first output voltage Vo1 of the first operational amplifier OP1 satisfies Equation (1).

$$V_{o1} = \left(1 + \frac{R_1}{R_2}\right) V_{s1} \quad (1)$$

In Equation (1), when the first and second resistors R1 and R2 are identical, the first output voltage Vo1 of the first operational amplifier OP1 may be twice the first voltage Vs1. Accordingly, the power supplying unit 130 may output the first output voltage Vo1 corresponding to twice the first power supply voltage Vs1 as a power supply voltage.

The filter unit 140 may include first and second filter units 141 and 142.

The first filter unit 141 includes a first filter resistor Rf1 connected between the first and third nodes N1 and N3, and a filter capacitor Cf connected between the third node N3 and the ground, and the second filter unit 142 includes a second filter resistor Rf2 connected between an output terminal of the first operational amplifier OP1 and a third node N3 and the filter capacitor Cf. In such a way, the first and second filter units 141 and 142 has a structure sharing the filter capacitor Cf.

In detail, the filter 140 not only performs a low pass filter (LPF) function to remove high frequency noise among input signals, but also determines signal response characteristics according to first and second time constant tau1 and tau2 respectively from the first and second filer units 141 and 142. In detail, a sensing voltage of the first node N1 and the first output voltage Vo1 of the first operational amplifier OP1 may have different degrees of exponential increase of the voltage of the third node N3 according to each of the time constants tau1 and tau2 of the first and second filter units 141 and 142, and may have a different cutoff frequency fc as a low pass filter.

Furthermore, the first time constant tau1 of the first filter unit 141 is defined as multiplication of the first filter resistance Rf1 and the filter capacitance Cf and the second time constant tau 2 of the second filter unit 142 is defined as multiplication of the second filter resistance Rf2 and the filter capacitance Cf. The first and second time constants tau1 and tau2 may be adjusted in consideration of resolution of a dryness degree.

The output unit 150 may receive the sensing voltage of the first node N1, which passes the filer unit 140 from the third node N3, and output the sensing voltage. The output unit 150 may include a second operational amplifier OP2, and the second operational amplifier OP2, of which an inverted terminal– and an output terminal are connected to each other and an non-inverted terminal+ is connected to the third node N3 to perform a voltage follower function, may output the voltage of the third node N3 to the output terminal as the second output voltage Vo2. In addition, the second operational amplifier OP2 may be driven by a second positive supplying voltage Vcc2+ and a second negative supplying voltage Vcc2–. In addition, the second negative supplying voltage Vcc2– may be 0 V. Therefore, the second operational amplifier OP2 may be driven as an operational amplifier for a signal power supply.

Furthermore, since measuring a large resistance component of several hundreds kΩ or greater, the sensing unit 110 is necessary to use an operational amplifier of which input impedance is close to infinite value. In this case, the cost may be reduced by configuring the second operational amplifier OP2 as a single power supply operational amplifier. In addition, the cost may be further reduced by allowing a separate voltage lower than a supplying voltage to the second operational amplifier OP2 to be supplied by the power supplying unit 130, and configuring the first operational amplifier OP1 of the power supplying unit 130 as a single power supply operational amplifier.

The voltage limiting unit 160 may include a first clamping diode DL1 of which a cathode electrode is connected to the output terminal of the first operational amplifier OP1 and an anode electrode is connected to the third node N3, and a second clamping diode DL2 of which a cathode electrode is connected to the third node N3 and an anode electrode is connected to the ground.

The voltage limiting unit 160 may allow the voltage of the third node N3 to satisfy Equation (2).

$$V_{N3} \leq V_{o1} + V_{th}(DL_1) \quad (2)$$

In other words, the voltage of the third node N3 may be allowed not to exceed a voltage that the first output voltage Vo1 of the first operational amplifier OP1 and a threshold voltage Vth of the first clamping diode DL1 are summed. At this point, the first output voltage Vo1 may be adjusted so that the voltage of the third node N3 does not exceed the second positive supplying voltage Vcc2+ in consideration of the second positive supplying voltage Vcc2+.

The protection unit 170 may include first and second output resistors Ro1 and Ro2, the first output resistor Ro1 may be connected between the output terminal of the second operational amplifier OP2 and a fourth node N4, and the second output resistor Ro2 may be connected between the fourth node N4 and the ground. The protection unit 170 divides the second voltage Vo1 of the output unit 150 through the first and second resistors Ro1 and Ro2 and output them to the fourth node N4 in order to reduce a signal to noise ratio and allow a voltage not greater than a measurement limit value of the measurement unit 200 to be input to the measurement unit 200.

Furthermore, the dryness sensing circuit 100 may further include an output capacitor Co connected between the fourth node N4 and the ground, and the output capacitor Co may function as a filter together with the output unit 150 to remove noise. In addition, the dryness sensing circuit 100 may further include an output diode D0 of which a cathode electrode is connected between the second voltage Vs2 and the fourth node N4. The output diode Do may allow the voltage of the fourth node N4 to satisfy Equation (3) and prevent the voltage of the fourth node N4 from being higher than the measurement limit value of the measurement unit 200 due to noise.

$$V_{N_4} \leq V_{o2} + V_{th}(D_o) \quad (3)$$

where Vth denotes a threshold voltage of the output diode Do.

The second power supply voltage Vs2 may have the same value as the value of the first power supply voltage Vs1, and the voltage value of the first and second power supply voltages Vs1 and Vs2 may be set as the same value as the voltage value according to the measurement limit value of the measurement unit 200, and the voltage value of the positive supplying voltages Vcc1+ and Vcc 2+ of the first and second operation amplifiers OP1 and OP2 may have higher values than the voltage value of the first and second power supply voltages Vs1 and Vs2.

<Sensing Performance Adjustment of a Damp Level According to Time Constants of the First and Second Filter Units>

Figure 6:
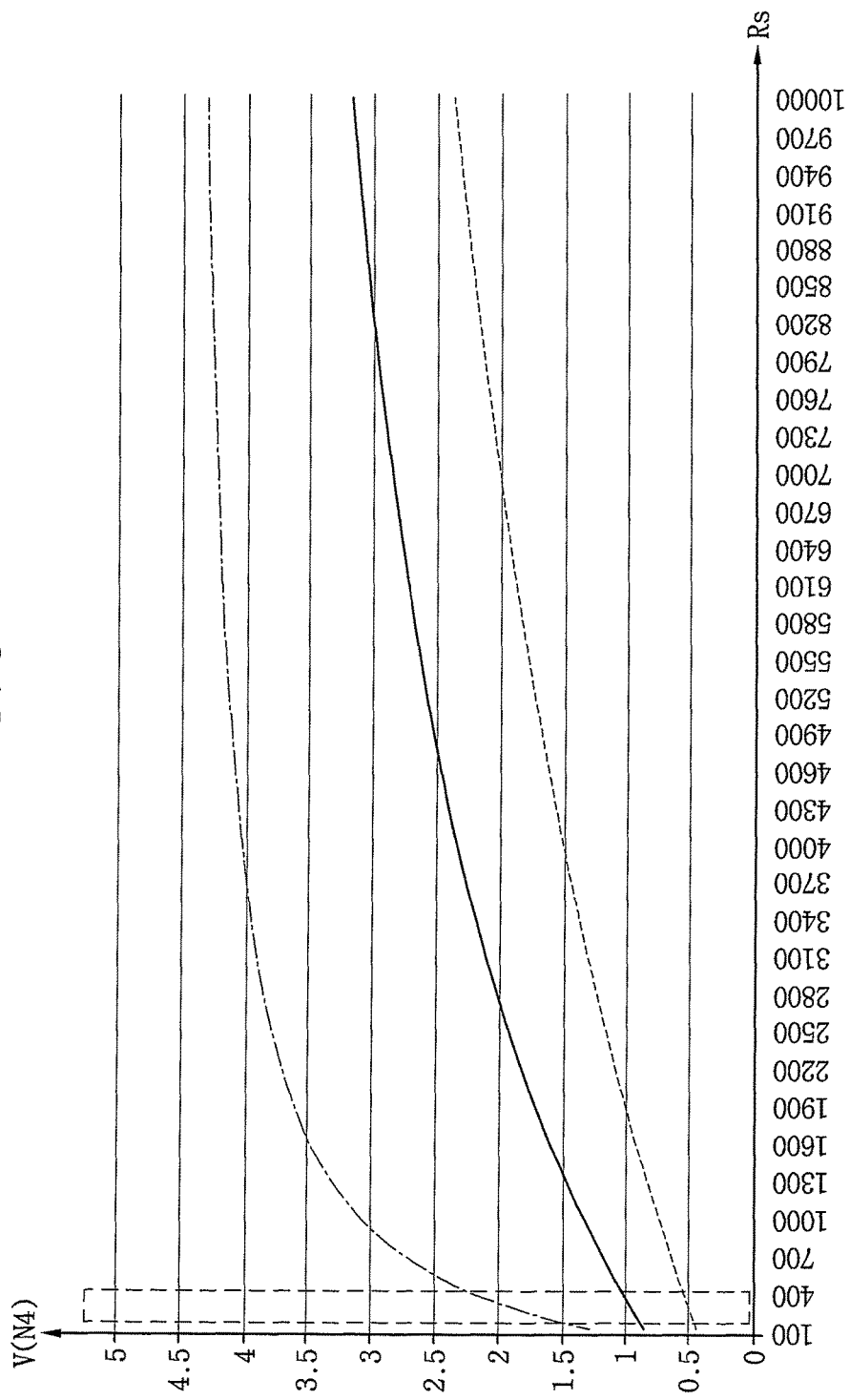
FIG. 6 shows a graph representing a voltage variation according to values of first and second filer resistors of first and second filter units.
Figure 7:
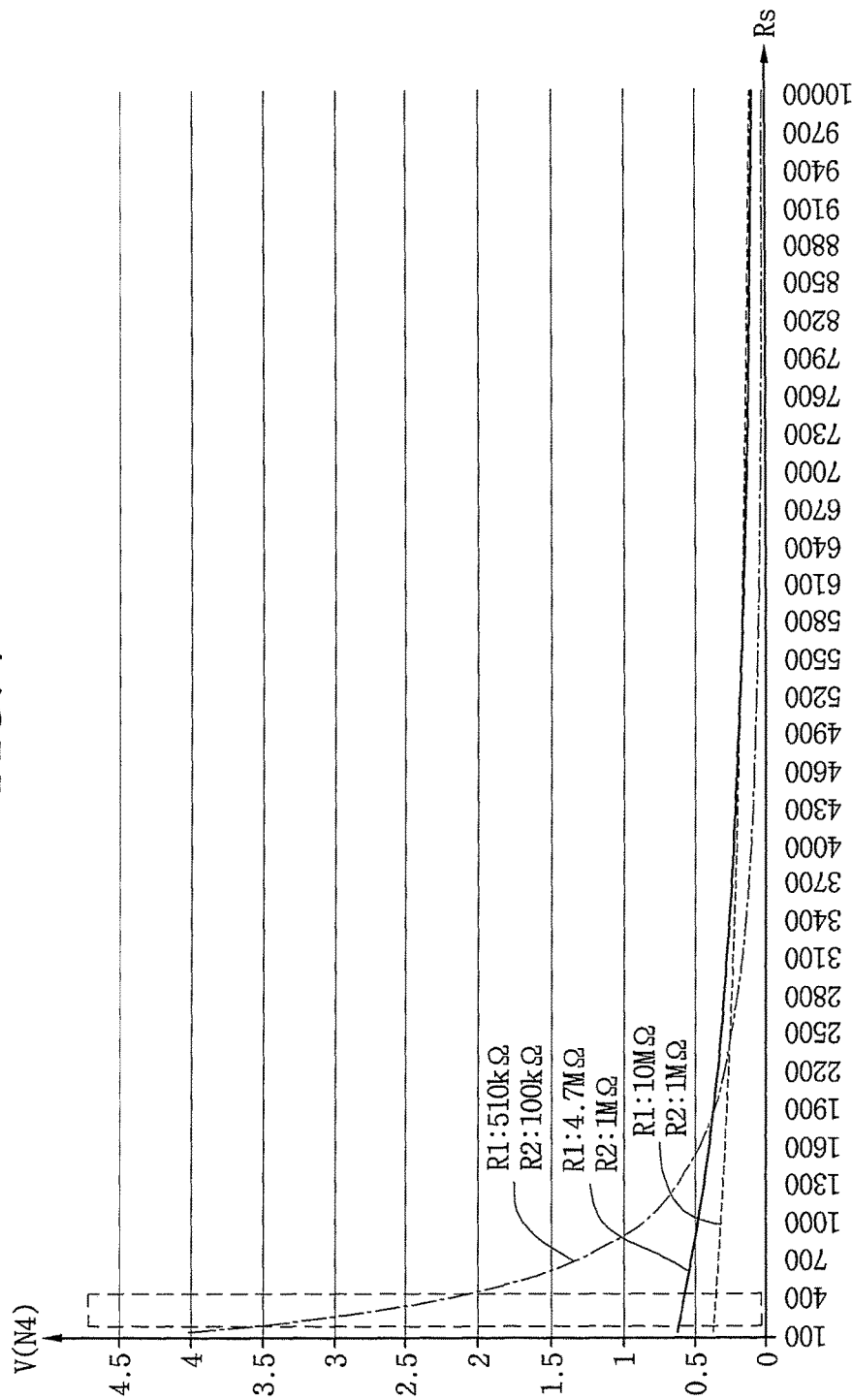
FIG. 7 shows a graph representing a voltage variation amount according to values of first and second filer resistors of first and second filter units.

FIG. 6 is a graph representing a voltage variation according to changes of first and second filter resistance values of the first and second filter units, and FIG. 7 is a graph representing a variation amount of a voltage according to changes of first and second filter resistance values of the first and second filter units.

In FIG. 6, a vertical axis denotes the voltage of the fourth node N4 and a horizontal axis denotes a resistance value (unit of kΩ) of the sensing resistor Rs.

| Power supply unit | | Static electricity prevention circuit | | Filter unit | |
|---|---|---|---|---|---|
| Vcc1+ | 13 V | C1 | 0.01 μF | Rf1 | Adjust |
| Vcc1− | 0 V | | | Rf2 | Adjust |
| R1 | 4.7 kΩ | C2 | 0.01 μF | f | 0.01 μF |
| R2 | 4.7 kΩ | | | | |

| Output unit | | Protection unit | | Output capacitor | |
|---|---|---|---|---|---|
| Vcc2+ | 13 V | Ro1 | 4.7 kΩ | Co | 0.01 μF |
| Vcc2− | 0 V | Ro2 | 3.9 kΩ | | |

In this case, element values and power supply voltages in the dryness sensing circuit 100 may have values shown in Table 1. In addition the measurement limit voltage of the measurement unit 200 is set as 5 V.

Referring to FIGS. 6 and 7, from a voltage variation of the fourth node N4 according to variation of values of the first and second filter resistors Rf1 and Rf2 of the first and second filter units 141 and 142, it may be seen that a damp side variation amount increases larger when the first filter resistance Rf1 is 510 kΩ and the second filer resistance Rf2 is 100 kΩ than when the first filter resistance Rf1 is 10 MΩ (or 4.7 MΩ) and the second filer resistance Rf2 is 1 MΩ In such a way, as the damp side variation amount increases larger, sensing performance of a damp side level may be improved among 5 dryness levels (namely, damp, less, normal, more, and very). In addition, the first and second filter resistances Rf1 and Rf2 are limited to the suggested ones. In a case where when the filter capacitance Cf is 0.01 μF, the first filter resistance Rf1 is larger than 100 kΩ and not greater than 1.5 MΩ and the second filter resistance Rf2 is larger than 10 kΩ and not greater than 500 kΩ, the time constant may be set as a small value enough to improve liquidity of a dryness determination algorithm and sensing performance of a damp side level may be improved.

<Reducing Distortion of a Sensing Signal According to Supplying Voltage Levels of the First and Second Operational Amplifiers and a Resistance Value of the Protecting Unit>

Figure 8:
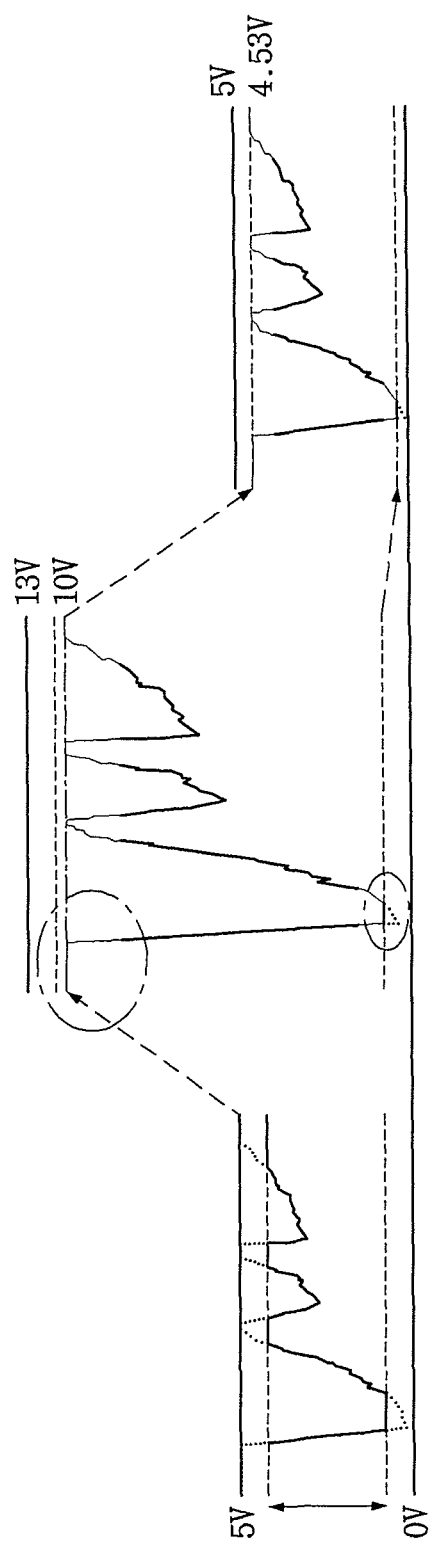
FIG. 8 is a waveform diagram representing distortion or not of a sensing signal according to supplying voltage levels of first and second operational amplifiers and a resistance value of a protection unit.

FIG. 8 is a waveform diagram representing distortion or not of a sensing signal according to supplying voltage levels of the first and second operational amplifiers and the resistance value of the protection unit.

Element values and power supply voltages in the dryness sensing circuit 100 may have values shown in Table 1. In addition the measurement limit voltage of the measurement unit 200 is set as 5 V.

Referring to FIG. 8, the first power supply voltage Vs1, which is 5 V, is not directly applied to the filter unit 140 but supplied through the power supplying unit 130 and the first power supply voltage Vs1 is amplified and 10 V is supplied to the filter unit 140. In addition, since the first and second operational amplifiers OP1 and OP2 are single power supply operation amplifiers, a width within which a sensing signal may swing may be increased from 0 V to 13 V and accordingly when the sensing signal swings within 0 V to 5 V, distortion around a peak value may be prevented (i.e., a dotted line portion). In addition, according to voltage division by the first and second output resistors Ro1 and Ro2 of the protection unit 170, 4.53 V output by dividing 10 V which is a peak value of the sensing signal with the protection unit 170 becomes a peak value of the sensing voltage input to the measurement unit 200 and is adjusted to the sensing voltage of the measurement limit voltage or smaller.

<Improvement of Voltage Fluctuation According to a Voltage Limiting Unit>

Figure 9:
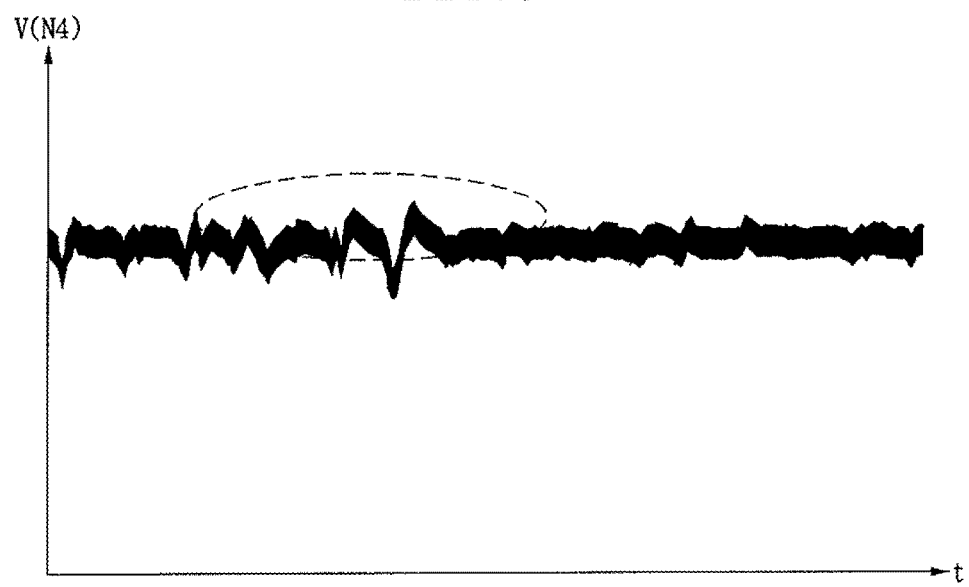
FIG. 9 is a graph representing a fourth node voltage of a dryness sensing circuit before addition of a voltage limiting unit.
Figure 10:
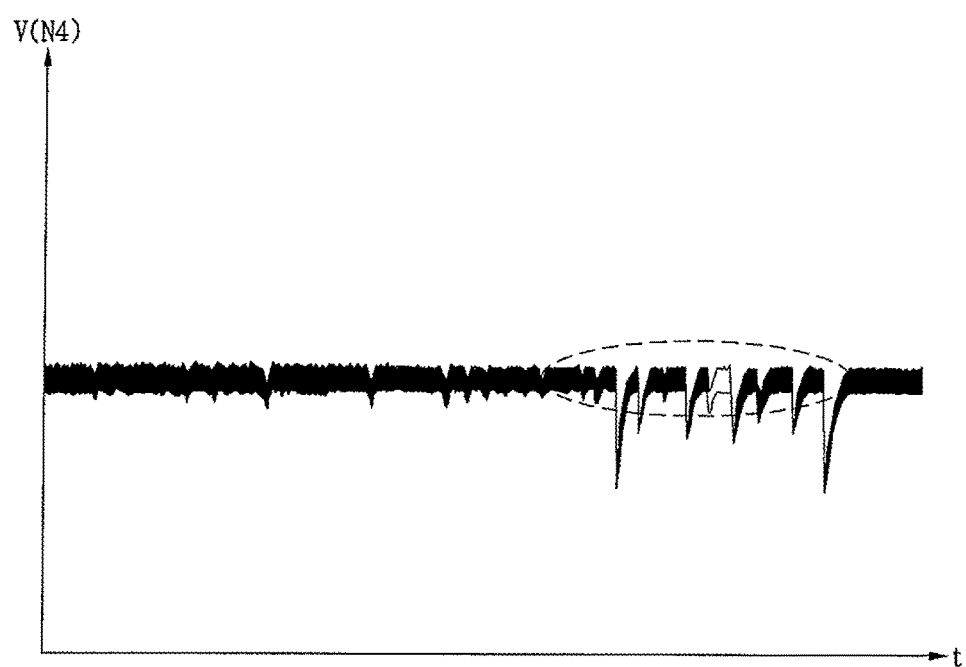
FIG. 10 is a graph representing a fourth node voltage of a dryness sensing circuit after addition of a voltage limiting unit.

FIG. 9 is a graph representing the fourth node voltage of the dryness sensing circuit before addition of the voltage limiting unit, and FIG. 10 is a graph representing the fourth node voltage of the dryness sensing circuit after addition of the voltage limiting unit.

Element values and power supply voltages in the dryness sensing circuit 100 may have values shown in Table 1. In addition the measurement limit voltage of the measurement unit 200 is set as 5 V.

Referring FIGS. 9 and 10, every time dried clothing contacts the sensing unit 110, the voltage of the fourth node N4 may fluctuate to exceed the measurement limit value of the measurement unit 200 (e.g., the dotted line). However, due to addition of the voltage limiting unit 170, the voltage of the fourth node N4 satisfy Equation (3) and, as shown as a dotted line in the graph, a phenomenon that the measurement limit value of the measurement unit 200 is exceeded may be improved.

Second Embodiment

Figure 11:
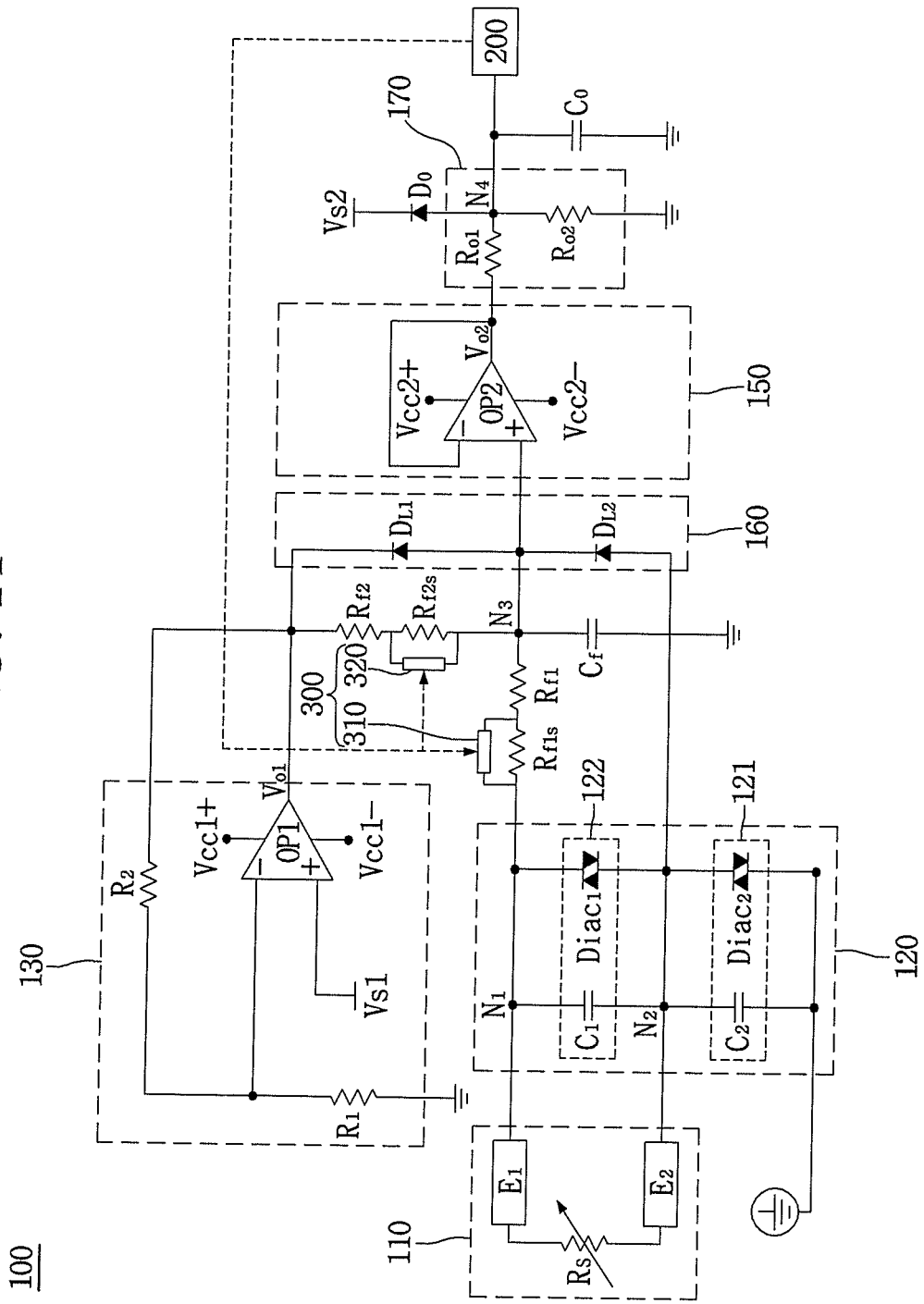
FIG. 11 is a dryness sensing circuit according to a second embodiment.
Figure 12:
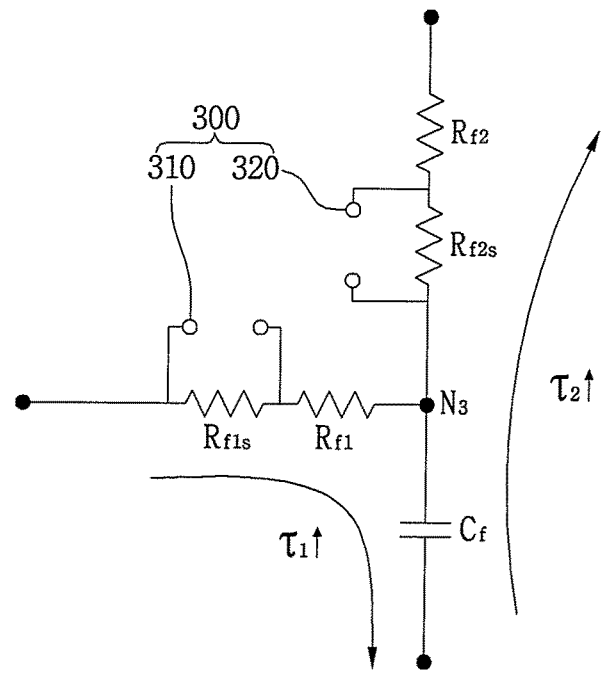
FIGS. 12 and 13 illustrate variations of a time constant according to an operation of the relay unit of FIG. 13.
Figure 13:
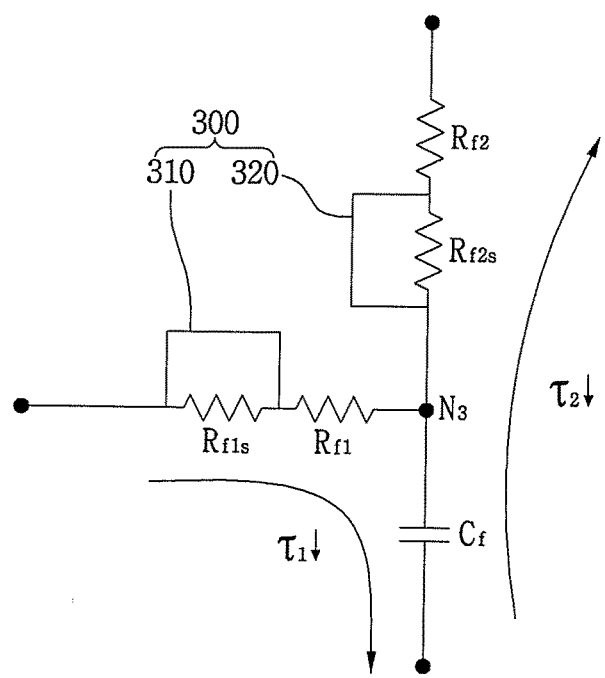

FIG. 11 illustrates a dryness sensing circuit according to a second embodiment, and FIGS. 12 and 13 are time constant changes according to an operation of a relay unit.

Referring FIG. 11, a dryness sensing circuit 100 according to a second embodiment, like the dryness sensing circuit 100 according to the first embodiment, may include a sensing unit 110, a static electricity protection unit 120, a power supplying unit 130, a filter unit 140, an output unit 150, a voltage limiting unit 160, and a protection unit 170.

The filter unit 140 may include first and second filter units 141 and 142, the first filter unit 141 may include a first auxiliary resistor Rf1s connected in serial to the first resistor Rf1 and a first relay unit 310 connected to both ends of the first auxiliary resistor Rf1s, and the second filter unit may include a second auxiliary resistor Rf2s connected in serial to the second resistor Rf2 and a second relay unit 320 connected to both ends of the second auxiliary resistor Rf2s.

The relay unit includes a relay switch element, and is an electric element performing a signal transfer function, which uses a principle that when a current is flowed through a coil wound iron core, the iron core becomes an electromagnet.

The relay unit 300 operates as a switch element, and may be turned on or off according to a control signal from the measurement unit 200. When the relay unit 300 is turned on and operates as a short circuit switch, since there appears an effect that a conducting wire is connect to both ends of the first and second auxiliary resistors Rf1s and Rf2s, the first and second auxiliary resistors Rf1s and Rf2s do not affect the first and second filter units 141 and 142, respectively. Furthermore, when the relay unit 300 is turned off and operates as an open switch, since there appears an effect that both ends of the first and second auxiliary resistors Rf1s and Rf2s are opened, the first auxiliary resistor Rf1s is serially connected to the first filter resistor Rf1 and there appears an effect of a serial resistor is added to the first filer resistor Rf1, and the second auxiliary resistor Rf2s is serially connected to the second filter resistor Rf2 and there appears an effect of a serial resistor is added to the second filer resistor Rf2. Therefore, a resistance value of a filter resistor included in the first and second filter units 141 and 142 may be increased. In addition, the relay unit 300 may be turned on by a high logic signal, and turned off by a low logic signal.

Figure 14:
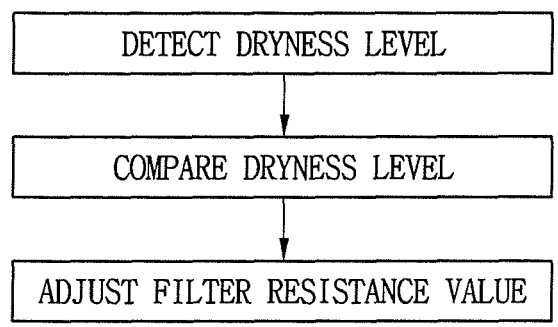
FIG. 14 illustrates an operation procedure of the dryness sensing circuit according to the second embodiment.
Figure 15:
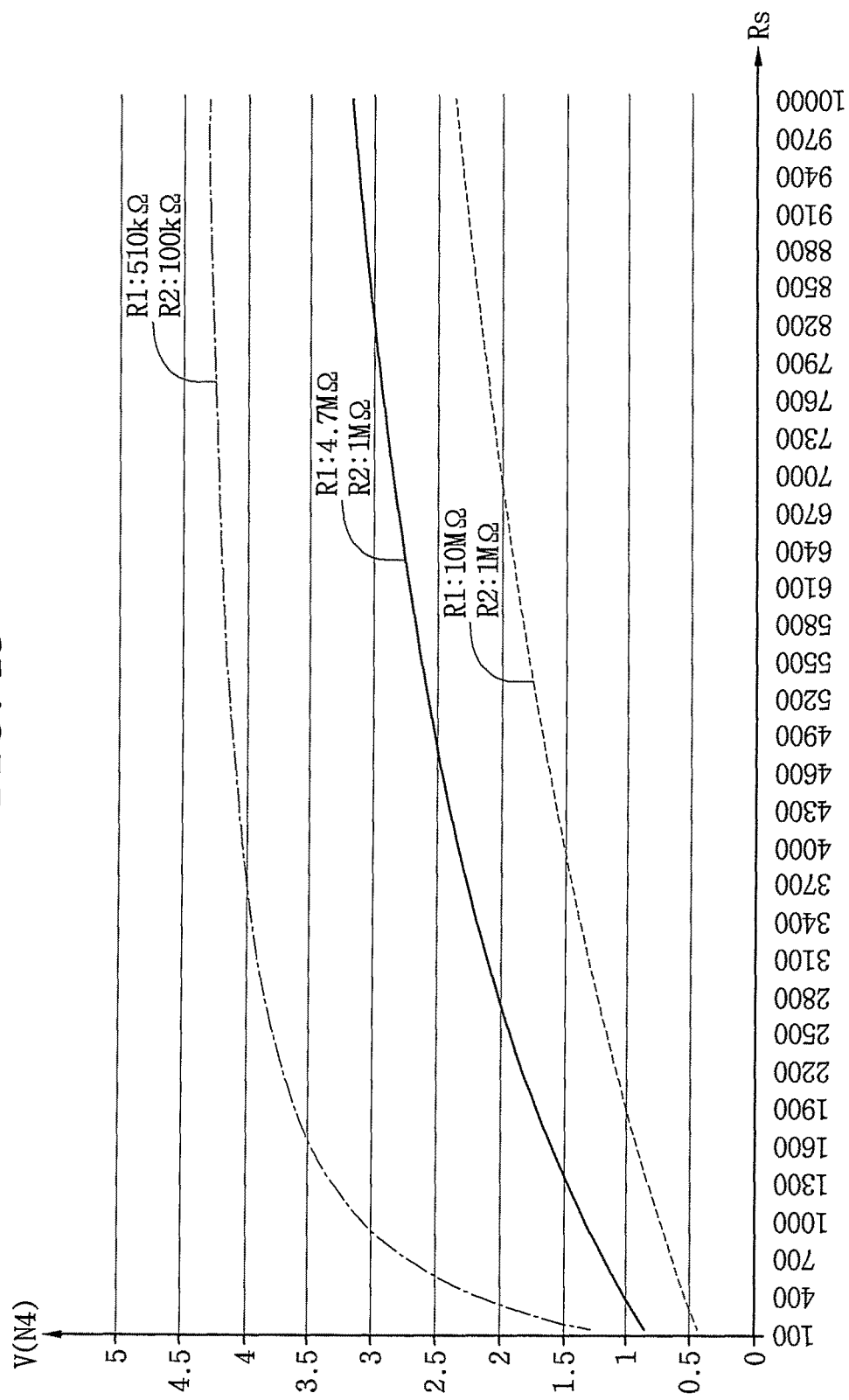
FIG. 15 is a graph representing a variation of a sensing voltage input to a measuring unit according to an operation of a relay unit.

FIG. 14 illustrates an operation procedure of the dryness sensing circuit according to the second embodiment. FIG. 15 is a graph representing a variation of a sensing voltage input to the measuring unit according to an operation of the relay unit.

Referring to FIGS. 14 and 15, a current dryness level of clothing which is a dry target is sensed by measuring moisture containment of the clothing through the measurement unit 200, the current dryness level is compared with a set dryness level, and according to the comparison result, time constants tau1 and tau2 of the first and second filter units 141 and 142 may be adjusted. In other words, the time constants tau1 and tau2 may be adjusted by comparing the moisture amount included in the dry target with a preset value.

For example, when a preset dryness level is a normal level as shown in FIG. 12, and a current dry level is a more level or a very level, the measurement unit 200 may provide a low level signal to the relay unit 300 to turn off the relay unit 300. Therefore, by making the time constants tau1 and tau2 of the first and second filter units 141 and 142 high, a variation amount is increased according to a resistance value of the sensing electrode 110 in the more and very levels and accordingly dryness resolution may be raised. In addition, as shown in FIG. 13, when a preset dryness level is a normal level and a current dry level is a less level or a damp level, the measurement unit 200 may provide a high level signal to the relay unit 300 to turn on the relay unit 300. Therefore, by making the time constants tau1 and tau2 of the first and second filter units 141 and 142 low, a variation amount is increased according to a resistance value of the sensing electrode 110 in the less and damp levels and accordingly dryness resolution may be raised.

Furthermore, each of the first and second relay units 310 and 320 may be individually controlled by the measurement unit 200, or controlled by a separate control means other than the measurement unit 200.

Third Embodiment

Figure 16:
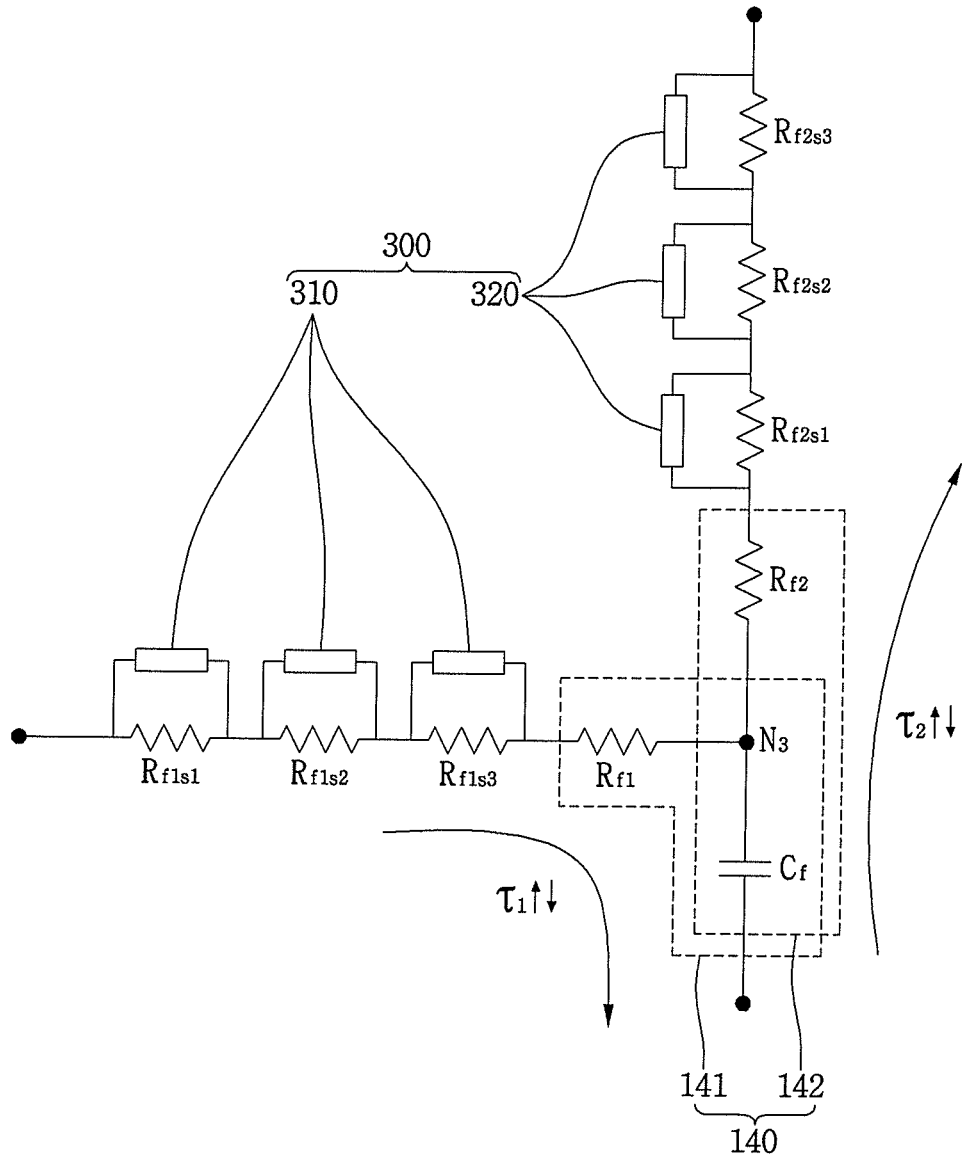
FIG. 16 illustrates a filter unit of a dryness sensing circuit according to a third embodiment.

FIG. 16 illustrates a filter unit of a dryness sensing circuit according to a third embodiment.

Referring to FIG. 16, a dryness sensing circuit 100 according to a third embodiment further includes an auxiliary resistor and a relay unit in addition to the filter unit 140 according to the second embodiment. In detail, the first filter unit 141 may include a plurality of first auxiliary resistors Rf1s1, Rf1s2, and Rf1s3 connected to the first filter resistor Rf1 in serial and connected to each other in serial, and a first relay unit 310 respectively connected to the plurality of first auxiliary resistors Rf1s1, Rf1s2, and Rf1s3 and the number of which being equal to the number of the plurality of first auxiliary resistors Rf1s1, Rf1s2, and Rf1s3. The second filter unit 142 141 may include a plurality of second auxiliary resistors Rf2s1, Rf2s2, and Rf2s3 connected to the second filter resistor Rf2 in serial and connected to each other in serial, and a second relay unit 320 respectively connected to the plurality of second auxiliary resistors Rf2s1, Rf2s2, and Rf2s3 and the number of which being equal to the number of the plurality of second auxiliary resistors Rf2s1, Rf2s2, and Rf2s3. Each of The first and second auxiliary resistors Rf1s1, Rf1s2, Rf1s3, Rf2s1, Rf2s2, and Rf2s3 may be individually controlled by the first and second relay units 310 and 320, and accordingly the time constants tau1 and tau2 of the first and second filter units 141 and 142 may be differed. In addition, by subdividing the preset dryness level, the time constants tau1 and tau2 of the first and second filter units 141 and 142 may be periodically adjusted according to moisture containment of clothing which is a dryness target.

In addition, the plurality number of first relay units 310 may sequentially operate to be open switches along the dryness of the dry target, and the plurality number of second relay units 320 may sequentially operate to be open switches along the dryness of the dry target. In other words, as the dry target is gradually dried, resistors serially and respectively added to the first and second filters Rf1 and Rf2 of the filter unit 140 are increased and accordingly the time constants tau1 and tau2 become gradually increased. In such a way, dryness resolution may be maintained optimally by adjusting the time constants tau1 and tau2 of the first and second filter units 141 and 142.

Furthermore, it is described that according to an operation of the relay unit 300, the auxiliary resistors Rf1s and Rf2s are respectively and serially added to the first and second filter resistors Rf1 and Rf2, but the embodiment is not limited hereto. The time constants of the filter unit 140 may be adjusted by adjusting resistance values according to a dryness degree of a dry target by making the first and second filter resistors Rf1 and Rf2 as variable resistors.

According to embodiments, by considering that a damp level is difficult to sense among the dryness levels, resistance value of the filter resistors Rf1 and Rf2 and capacitance value of the capacitor Cf optimized to the damp level may be determined, a voltage division may be used through output resistors Ro1 and Ro2 of the static electricity prevention unit 120 and the output unit 170 in order to minimize an effect of a signal to noise ratio according to reduction in a value of the first filter resistor Rf1, and a manufacturing cost may be reduced by using, as a single power supply operational amplifier, an operational amplifier of which input impedance is close to infinite value, which is prepared for detecting a dry target having several hundreds kΩ In addition, according to dryness of the dry target, by changing values of the first and second filter resistors Rf1 and Rf2, the time constants of the filter unit 140 may be adjusted and accordingly optimal dryness resolution can be implemented for each dryness level.

According to the dryness sensing circuit and dryness sensing method according to an embodiment, a time constant of a resistor and capacitor can be set short and a noise effect of a power supply can be minimized for liquidity of a dryness algorithm, an operational amplifier of which input impedance is very high is used for measuring a dryness degree of dry target having a large resistance of several hundreds kΩ or higher, a single power supply operational amplifier can be used for cost reduction, an optimal element value can be matched with an internal element value for raising dryness resolution in a damp level, a sensing voltage level can be adjusted in consideration of a measurement limit value of a measuring unit, and dryness sensing capability can be improved by adjusting sensing sensitivity in a dry level according to a dryness level.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A dryness sensing circuit comprising:
   a first sensing electrode connected to a first node;
   a second sensing electrode connected to a second node;
   a non-inverting amplifier that includes an inverting terminal, a non-inverting terminal to supply a first power supply voltage, and an output terminal to output a first output voltage;
   a filter device comprising a first filter resistor connected between the first node and a third node, a filter capacitor connected between the third node and a ground, and a second filter resistor connected between the output terminal and the third node;
   a voltage follower to provide a second output voltage based on a voltage at the third node; and
   a voltage limiter comprising a first diode and a second diode, the first diode having a cathode terminal connected to the output terminal of the non-inverting amplifier and an anode terminal connected to the third node, and the second diode having a cathode terminal connected to the third node and an anode terminal connected to the ground,
   wherein a dryness level of a dry target is to be determined based at least on the second output voltage, and
   wherein the voltage at the third node is lower than a sum voltage of the first output voltage and a threshold voltage of the first diode.

2. The dryness sensing circuit of claim 1, wherein the first filter resistor has a value greater than about 100 kΩ and not greater than about 1.5 MΩ,
   the second filter resistor has a value greater than about 10 kΩ and not greater than about 500 kΩ, and
   the filter capacitor has a value of about 0.01 μF.

3. The dryness sensing circuit of claim 1, further comprising a static electricity protection unit comprising a first capacitor and a first diac connected together in parallel and connected between the first node and the ground, and a second capacitor and a second diac connected to each other in parallel and connected between the ground and earth ground.

4. The dryness sensing circuit of claim 1, wherein the non-inverting amplifier and the voltage follower are single power supply operational amplifiers.

5. The dryness sensing circuit of claim 4, wherein the non-inverting amplifier includes first and second resistors connected to the inverting terminal and having an identical resistance value.

6. The dryness sensing circuit of claim 5, further comprising a measurement unit for measuring the second output voltage, wherein the first power supply voltage is a voltage value identical to a measurement limit value of the measurement unit.

7. The dryness sensing circuit of claim 1, further comprising a protection unit comprising a first output resistor connected between an output terminal of the voltage follower and a fourth node, and a second output resistor connected between the fourth node and the ground.

8. The dryness sensing circuit of claim 7, further comprising an output diode having a cathode terminal connected to a second power supplying terminal and an anode terminal connected to the fourth node; and
an output capacitor connected between the fourth node and the ground.

9. The dryness sensing circuit of claim 8, wherein a second power supply voltage from the second power supply terminal is identical to the first power supply voltage.

10. A dryness sensing circuit comprising:
a first sensing electrode connected to a first node;
a second sensing electrode connected to a second node;
a non-inverting amplifier that includes an inverting terminal, a non-inverting terminal to supply a first power supply voltage, and an output terminal to output a first output voltage;
a first filter device and a second filter device, wherein the first filter device includes a first filter resistor connected between the first node and a third node, a first auxiliary resistor connected between the first filter resistor and the third node, a first relay unit connected to both ends of the first auxiliary resistor, a filter capacitor connected between the third node and a ground, and the second filter device includes a second filter resistor connected between the output terminal and the third node, a second auxiliary resistor connected between the second filter resistor and the third node, and a second relay unit connected to both ends of the second auxiliary resistor;
a voltage follower to provide a second output voltage based on a voltage at the third node; and
a voltage limiter that includes a first diode and a second diode, the first diode having a cathode terminal connected to the output terminal of the non-inverting amplifier and an anode terminal connected to the third node, and the second diode having a cathode terminal connected to the third node and an anode terminal connected to the ground,
wherein a dryness level of a dry target is to be determined based at least on the second output voltage, and
wherein the voltage at the third node is lower than a sum voltage of the first output voltage and a threshold voltage of the first diode.

11. The dryness sensing circuit of claim 10, wherein a resistance value of the first filter device is to vary based on whether the first relay unit is turned on, and a resistance value of the second filter device is to vary based on whether the second relay unit is turned on.

12. The dryness sensing circuit of claim 10, wherein a resistance value of the first filter device is a sum resistance value of the first filter resistor and the first auxiliary resistor when the first relay unit is turned on, and is a resistance value of the first filter resistor when the first relay unit is turned off.

13. The dryness sensing circuit of claim 10, wherein a resistance value of the second filter device is a sum resistance value of the second filter resistor and the second auxiliary resistor when the second relay unit is turned on, and is a resistance value of the second filter resistor when the second relay unit is turned off.

14. The dryness sensing circuit of claim 10, further comprising a measurement unit for measuring the second output voltage,
wherein the first power supply voltage is a voltage value identical to a measurement limit value of the measurement unit, and
wherein the measurement unit to control switching operation for each of the first and second relay units.

* * * * *